(12) United States Patent
Wang et al.

(10) Patent No.: US 10,717,813 B2
(45) Date of Patent: Jul. 21, 2020

(54) PHOTOCROSSLINKABLE POLY(CAPROLACTONE FUMARATE)

(71) Applicant: Mayo Foundation for Medical Education and Research, Rochester, MN (US)

(72) Inventors: Shanfeng Wang, Knoxville, TN (US); Lichun Lu, Rochester, MN (US); Michael J. Yaszemski, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/000,833

(22) Filed: Jan. 19, 2016

(65) Prior Publication Data
US 2016/0199536 A1 Jul. 14, 2016

Related U.S. Application Data

(62) Division of application No. 11/718,906, filed as application No. PCT/US2005/040571 on Nov. 10, 2005, now Pat. No. 9,255,178.

(60) Provisional application No. 60/627,079, filed on Nov. 12, 2004.

(51) Int. Cl.
| | |
|---|---|
| C08L 67/00 | (2006.01) |
| C08G 63/91 | (2006.01) |
| A61L 27/54 | (2006.01) |
| A61L 27/56 | (2006.01) |
| A61L 27/18 | (2006.01) |
| A61L 27/46 | (2006.01) |
| C08G 63/08 | (2006.01) |
| C08L 67/06 | (2006.01) |

(52) U.S. Cl.
CPC ............ *C08G 63/912* (2013.01); *A61L 27/18* (2013.01); *A61L 27/46* (2013.01); *A61L 27/54* (2013.01); *A61L 27/56* (2013.01); *C08G 63/08* (2013.01); *C08L 67/06* (2013.01)

(58) Field of Classification Search
CPC ...... A61L 31/16; A61L 24/0042; C08L 67/06; C08L 67/00; C08G 63/08; A61F 2002/2835; A61K 38/1875; C08F 267/06
See application file for complete search history.

(56) References Cited

U.S. PATENT DOCUMENTS

| | | |
|---|---|---|
| 4,082,816 A | 4/1978 | Fisk et al. |
| 4,668,295 A | 5/1987 | Bajpai |
| 4,722,948 A | 2/1988 | Sanderson |
| 5,085,861 A | 2/1992 | Gerhart et al. |
| 5,490,962 A | 2/1996 | Cima et al. |
| 5,514,378 A | 5/1996 | Mikos |
| 5,518,680 A | 5/1996 | Cima |
| 5,527,864 A | 6/1996 | Suggs et al. |
| 5,644,005 A | 7/1997 | Suggs et al. |
| 5,733,951 A | 3/1998 | Yaszemski et al. |
| 5,747,605 A | 5/1998 | Breant et al. |
| 5,780,426 A | 7/1998 | Palladino |
| 5,786,217 A | 7/1998 | Tubo et al. |
| 5,869,170 A | 2/1999 | Cima et al. |
| 5,908,782 A | 6/1999 | Marshak et al. |
| 6,124,373 A | 9/2000 | He et al. |
| 6,153,664 A | 11/2000 | Wise et al. |
| 6,271,278 B1 | 8/2001 | Park et al. |
| 6,281,256 B1 | 8/2001 | Harris et al. |
| 6,306,821 B1 | 10/2001 | Mikos |
| 6,355,755 B1 | 3/2002 | Peter et al. |
| 6,379,962 B1 | 4/2002 | Holy et al. |
| 6,384,105 B1 | 5/2002 | He et al. |
| 6,395,300 B1 | 5/2002 | Straub et al. |
| 6,423,790 B1 | 7/2002 | He et al. |
| 6,436,426 B1 | 8/2002 | Liao et al. |
| 6,454,811 B1 | 9/2002 | Sherwood et al. |
| 6,530,958 B1 | 3/2003 | Cima |
| 6,562,374 B1 | 5/2003 | Han et al. |
| 6,673,285 B2 | 1/2004 | Ma |
| 6,753,358 B2 | 6/2004 | Fisher et al. |
| 6,759,485 B2 | 7/2004 | He et al. |
| 6,884,432 B2 | 4/2005 | Yaszemski et al. |
| 6,884,778 B2 | 4/2005 | Jo et al. |
| 7,189,413 B2 | 3/2007 | Calias |

(Continued)

FOREIGN PATENT DOCUMENTS

| | | |
|---|---|---|
| CA | 1136317 | 11/1982 |
| EP | 0000507 | 2/1979 |

(Continued)

OTHER PUBLICATIONS

Storey et al "Bioabsorbable composites. I: Fundamental design considerations using free radically crosslinkable matrices", vol. 14, Issue 1, Feb. 1993, pp. 7-16.*

(Continued)

*Primary Examiner* — Gregory Listvoyb
(74) *Attorney, Agent, or Firm* — Fish & Richardson P.C.

(57) ABSTRACT

Fumaric acid or a salt thereof, such as a fumaryl halide (e.g. fumaryl chloride), which contains unsaturated carbon-carbon double bonds that can be used for in situ crosslinking, is copolymerized with poly(caprolactone) diol in the presence of an alkali metal salt. The resulting photocrosslinkable biocompatible and bioresorbable poly(caprolactone fumarate) biomaterial is useful in the fabrication of injectable an in-situ hardening scaffolds for application in skeletal reconstruction.

16 Claims, 5 Drawing Sheets

(56) References Cited

U.S. PATENT DOCUMENTS

| | | |
|---|---|---|
| 7,309,232 B2 | 12/2007 | Rutherford et al. |
| 7,595,043 B2 | 9/2009 | Hedrick et al. |
| 7,629,388 B2 | 12/2009 | Mikos et al. |
| 7,642,300 B2 | 1/2010 | Yaszemski |
| 7,816,461 B2 | 10/2010 | Wang et al. |
| 8,343,527 B2 | 1/2013 | Dadsetan |
| 8,912,247 B2 | 12/2014 | Wang et al. |
| 9,255,178 B2 * | 2/2016 | Wang ............ A61L 27/18 |
| 2001/0009662 A1 | 7/2001 | Cohn et al. |
| 2001/0039453 A1 | 11/2001 | Gresser et al. |
| 2001/0048945 A1 | 12/2001 | Sankaram |
| 2002/0028189 A1* | 3/2002 | Jo ............ A61K 47/48215 424/78.3 |
| 2002/0177668 A1 | 11/2002 | He et al. |
| 2003/0032733 A1 | 2/2003 | Fisher et al. |
| 2003/0152548 A1 | 8/2003 | Mikos et al. |
| 2004/0054410 A1 | 3/2004 | Barrows |
| 2005/0019371 A1 | 1/2005 | Anderson et al. |
| 2005/0058632 A1 | 3/2005 | Hedrick et al. |
| 2005/0079470 A1 | 4/2005 | Rutherford et al. |
| 2005/0209704 A1 | 9/2005 | Maspero et al. |
| 2005/0251267 A1 | 11/2005 | Winterbottom et al. |
| 2007/0043202 A1 | 2/2007 | Yaszemski et al. |
| 2008/0125870 A1 | 5/2008 | Carmichael et al. |
| 2008/0194792 A1 | 8/2008 | Wang et al. |
| 2008/0206308 A1 | 8/2008 | Jabbari |
| 2013/0331869 A1 | 12/2013 | Runge et al. |

FOREIGN PATENT DOCUMENTS

| | | |
|---|---|---|
| EP | 1252196 | 11/2005 |
| EP | 0877033 | 9/2007 |
| GB | 1394396 | 5/1975 |
| JP | H11-060716 | 3/1999 |
| JP | 2002-542352 | 12/2002 |
| JP | 2003-103905 | 4/2003 |
| JP | 2003-182208 | 7/2003 |
| WO | WO 1995/029710 | 11/1995 |
| WO | WO 2001/085180 | 11/2001 |
| WO | WO 2002/062357 | 8/2002 |
| WO | WO 2003/033563 | 4/2003 |
| WO | WO 2005/004811 | 1/2005 |
| WO | WO 2005/020849 | 3/2005 |
| WO | WO 2006/053031 | 5/2006 |

OTHER PUBLICATIONS

Kweon et al "A novel degradable polycaprolactone networks for tissue engineering", Biomaterials, vol. 24, issue 5, Feb. 2003, pp. 801-808.*

Ackery, "A global perspective on spinal cord injury epidemiology," *J. Neurotrauma*, 21(10):1355-1370, Oct. 2004.

Ahlborn et al., "One hour electrical stimulation accelerates functional recovery after femoral nerve repair," *Exp Neurol.*, 208(1):137-144, Epub Aug. 23, 2007.

Anseth et al., "Photopolymerizable degradable polyanhydrides with osteocompatibility," *Nat Biotechnol.*, 17(2):156-159, Feb. 1999.

Arino et al., "Implantation of Schwann cells in rat tendon autografts as a model for peripheral nerve repair: long term effects on functional recovery," *Scand J Plast Reconstr Surg Hand Surg.*, 42(6):281-285, 2008.

Ashley et al., "Therapeutic stimulation of denervated muscles: The influence of pattern," *Muscle Nerve*, 38(1):875-886, Jul. 2008.

Baltrusaitis et al., "Reactions of sulfur dioxide on calcium carbonate single crystal and particle surfaces at the adsorbed water carbonate interface," *Phys Chem Chem Phys.*, 9(23):3011-3024, Epub Feb. 28, 2007.

Behravesh and Mikos, "Three-dimensional culture of differentiating marrow stromal osteoblasts in biomimetic poly(propylene fumarate-co-ethylene glycol)-based macroporous hydrogels," *J Biomed Mater Res A*, 66(3):698-706, Sep. 1, 2003.

Chen et al., "Template synthesis of the polypyrrole tube and its bridging in vivo sciatic nerve regeneration," *J. Mat. Sci. Lett.*, 19(23):2157-2159, Nov. 2000.

Chun et al., "Controlled release of plasmid DNA from biodegradable scaffolds fabricated using a thermally-induced phase-separation method," J. Biomater. Sci. Polymer Ed., 15(11):1341-1353, 2004.

Chung et al., "Syntheses and evaluation of biodegradable multifunctional polymer networks," *Eur Pol J*, 39(9):1817-1822, Sep. 2003.

Cui et al., "Advances in stem cell transplantation for spinal cord injury," *Journal of Clinical Rehabilitative Tissue Engineering Research*, 12:9335-9338, 2008.

Dadsetan et al., "Surface chemistry mediates adhesive structure, cytoskeletal organization, and fusion of macrophages," *J Biomed Mater Res A.*, 71(3):439-448, Dec. 1, 2004.

De Ruiter et al., "Methods for in vitro characterization of multichannel nerve tubes," *J Biomed Mater Res A.*, 84(3):643-651, Mar. 1, 2008.

De Ruiter et al., "Misdirection of regenerating motor axons after nerve injury and repair in the rat sciatic nerve model," *Exp Neurol.*, 211(2):339-350, Epub Jan. 8, 2008.

De Ruiter, "Accuracy of motor axon regeneration across autograft, single-lumen, and multichannel poly(lactic-co-glycolic acid) nerve tubes," *Neurosurgery*, 63(1):144-153; discussion 153-155, Jul. 2008.

Elfick, "Poly(epsilon-caprolactone) as a potential material for a temporary joint spacer," *Biomaterials*, 23(23):4463-4467, Dec. 2002.

Fisher et al., "Photoinitiated cross-linking of the biodegradable polyester poly(propylene fumarate). Part I. Determination of network structure," *Biomacromolecules.*, 4(5):1327-1334, Sep.-Oct. 2003.

George, "Novel polypyrrole derivatives to enhance conductive polymer-tissue interactions," Thesis dissertation, MIT, Oct. 19, 2005, 1-145.

Geremia et al., "Electrical stimulation promotes sensory neuron regeneration and growth-associated gene expression," *Exp Neurol.*, 205(2):347-359, Epub Feb. 21, 2007.

Gomez and Schmidt, "Nerve growth factor-immobilized polypyrrole: bioactive electrically conducting polymer for enhanced neurite extension," *J Biomed Mater Res A.*, 81(1):135-149, Apr. 2007.

Han et al., "Synthesis and characterization of crosslinked polymers for biomedical composites" *Journal of Macromolecular Science: Part A—Chemistry*, 25(5-7): 847-869, 1988.

Hedberg et al., "Controlled Release of an Osteogenic Peptide from Injectable Biodegradable Polymeric Composites," *J. Control. Release*, 84,137-150, 2002.

Hiremath et al., "Simple setup to measure electrical properties of polymeric films," *Review of Scientific Instruments*, 77(12), 2006.

Holland et al., "In vitro release of transforming growth factor-b1 from gelatin microparticles encapsulated in biodegradable, injectable oligo(poly(ethylene glycol) fumarate) hydrogels," *J Control Release.*, 91(3):299-313, Sep. 4, 2003.

Huang et al., "Synthesis and characterization of electroactive and biodegradable ABA block copolymer of polylactide and aniline pentamer," *Biomaterials*, 28(10):1741-1751, Epub Jan. 10, 2007.

Huang et al., "Synthesis of biodegradable and electroactive multiblock polylactide and aniline pentamer copolymer for tissue engineering applications," *Biomacromolecules*, 9:850-858, 2008.

Hutmacher et al., "Scaffold-based tissue engineering: rationale for computer-aided design and solid free-form fabrication systems," *Trends in Biotech*, 22(7):354-362, Jul. 2004.

Jabbari et al., "Development of a novel self-crosslinkable poly (caprolactone fumarate) as a biodegradable and injectable scaffold for bone tissue engineering," Proceedings of the 25th Annual International Conference of the IEEE Engineering in Medicine and Biology Society, 2:1219-1222, 2003.

Jabbari et al., "Synthesis, material properties, and biocompatibility of a novel self-crosslinkable poly(caprolactone fumarate) as an injectable tissue engineering scaffold," *Biomacromolecules*, 6(5):2503-2511, Sep.-Oct. 2005.

(56) References Cited

OTHER PUBLICATIONS

Jo et al., "Modification of oligo(poly(ethylene glycol) fumarate) macromer with a GRGD peptide for the preparation of functionalized polymer networks," *Biomacromolecules*, 2(1):255-261, Spring 2001.
Jo et al., "Synthesis and Characterization of Oligo(poly(ethylene glycol) fumarate) Macromer," *Macromolecules*, 34(9): 2839-2844, 2001.
Kam et al., "Electrical stimulation of neural stem cells mediated by humanized carbon nanotube composite made with extracellular matrix protein," *Nano Lett.*, 9(1):273-278, Jan. 2009.
Kemp et al., "Growth factor and stem cell enhanced conduits in peripheral nerve regeneration and repair," *Neurol Res.*, 30(10):1030-1038, Dec. 2008.
Kotwal and Schmidt, "Electrical stimulation alters protein adsorption and nerve cell interactions with electrically conducting biomaterials," *Biomaterials*, 22(10):1055-1064, May 2001.
Kweon et al., "A novel degradable polycaprolactone networks for tissue engineering," *Biomaterials.*, 24(5):801-808, Feb. 2003.
Lang et al., "Functionalized multiarm poly(epsilon-caprolactone)s: Synthesis, structure analysis, and network formation," *J. Applied Polymer Science*, 86(9):2296-2306, ePub Sep. 18, 2002.
Lee et al., "Carboxy-endcapped conductive polypyrrole:biomimetic conducting polymer for cell scaffolds and electrodes," *Langmuir*, 22(24):9816-9819, Nov. 21, 2006.
Lee, "Carboxylic acid-functionalized conductive polypyrrole as a bioactive platform for cell adhesion," *Biomacromolecules*, 7(6):1692-1695, Jun. 2006.
Li et al., "Direct-current electrical field guides neuronal stem/progenitor cell migration," *Stem Cells*, 26(8):2193-2200, Epub Jun. 12, 2008.
Mao et al., "New biocompatible polypyrrole-based films with good blood compatibility and high electrical conductivity," *Colloids Surf B Biointerfaces*, 67(1):41-45, Epub Aug. 3, 2008.
Moore et al., "Multiple-channel scaffolds to promote spinal cord axon regeneration," *Biomaterials*, 27(3):419-429, Epub Aug. 31, 2005.
Ng et al., "Evaluation of ultra-thin poly(epsilon-caprolactone) films for tissue-engineered skin," *Tissue Eng.*, 7(4):441-455, Aug. 2001.
Park et al., "Characterization of porous collagen/hyaluronic acid scaffold modified by 1-ethyl-3-(3-dimethylaminopropyl)carbodiimide cross-linking," *Biomaterials*, 23(4):1205-1212, Feb. 15, 2002.
Park et al., "Electrical pulsed stimulation of surfaces homogeneously coated with gold nanoparticles to induce neurite outgrowth of PC12 cells," *Langmuir*, 25(1):451-457, Jan. 6, 2009.
Payne et al., "Development of an injectable, in situ crosslinkable, degradable polymeric carrier for osteogenic cell populations. Part 3. Proliferation and differentiation of encapsulated marrow stromal osteoblasts cultured on crosslinking poly(propylene fumarate)," *Biomaterials*, 23(22): 4359-4371, Nov. 2002.
Peter et al., "Crosslinking characteristics of an injectable poly(propylene fumarate)/beta-tricalcium phosphate paste and mechanical properties of the crosslinked composite for use as a biodegradable bone cement" *J Biomed Mater Res.*, 44(3):314-321, Mar. 5, 1999.
Runge et al., "Fabrication of conducting composite materials of polypyrrole-polycaprolactone fumarate for nerve regeneration," *Polymer Preprints*, 50(1):313-314, 2009.
Sago et al., "In vitro differentiation of canine celiac adipose tissue-derived stromal cells into neuronal cells,"*J Vet Med Sci.*, 70(4):353-357, Apr. 2008.
Schmidt et al., "Stimulation of neurite outgrowth using an electrically conducting polymer," *Proc Natl Acad Sci U S A.*, 94(17):8948-8953, Aug. 19, 1997.
Shi et al., "A novel electrically conductive and biodegradable composite made of polypyrrole nanoparticles and polylactide," *Biomaterials*, 25(13):2477-2488, Jun. 2004.
Shi et al., "Electrical stimulation enhances viability of human cutaneous fibroblasts on conductive biodegradable substrates," *J Biomed Mater Res A.*, 84(4):1026-1037, Mar. 15, 2008.
Shi et al., "The regulation of cell functions electrically using biodegradable polypyrrole-polylactide conductors," *Biomaterials*, 29(28):3792-3798, Epub Jul. 7, 2008.
Shin et al., "In vivo bone and soft tissue response to injectable, biodegradable oligo(poly(ethylene glycol) fumarate) hydrogels," *Biomaterials.*, 24(19):3201-3211, Aug. 2003.
Shin et al., "Modulation of marrow stromal osteoblast adhesion on biomimetic oligo[poly(ethylene glycol) fumarate] hydrogels modified with Arg-Gly-Asp peptides and a poly(ethyleneglycol) spacer," *J Biomed Mater Res.*, 61(2):169-179, Aug. 2002.
Shustak et al., "A novel electrochemically synthesized biodegradable thin film of polypyrrole-polyethyleneglycol-polylactic acid nanoparticles," *New J. Chem.*, 31(1):163-168, 2007.
Song et al., "Peripheral Nerve: What's New in Basic Science Laboratories," *Neurosurg Clin N Am.*, 20(1):121-131, Jan. 2009.
Storey et al., "Synthesis and free radical curing of poly(epsilon-caprolactone-co-D,L-lactide) fumamte" Polymer Preprints, Division of Polymer Chemistry, Inc, American Chemical Society, 32(1):629-630, 1991.
Storey et al., "Bioabsothable composites I. Fundamental design considerations using free radically crosslinkable matrices," *Polymer Composites*, 14(1):7-16, Feb. 1993.
Tabesh, "The role of biodegradable engineered scaffolds seeded with Schwann cells for spinal cord regeneration," *Neurochem Int.*, 54(2):73-83, Epub Nov. 25, 2008.
Taylor et al., "The incidence of peripheral nerve injury in extremity trauma," *Am J Phys Med Rehabil.*, 87(5):381-385, May 2008.
Temenoff et al., "Effect of poly(ethylene glycol) molecular weight on tensile and swelling properties of oligo(poly(ethylene glycol) fumarate) hydrogels for cartilage tissue engineering," *J. Biomedical Material Research*, 59(3), 429-437, 2001.
Temenoff et al., "Thermally cross-linked oligo(poly(ethylene glycol) fumarate) hydrogels support osteogenic differentiation of encapsulated marrow stromal cells in vitro," *Biomacromolecules*, 5(1):5-10, published online on Nov. 26, 2003.
Vivó et al., "Immediate electrical stimulation enhances regeneration and reinnervation and modulates spinal plastic changes after sciatic nerve injury and repair," *Exp Neurol.*, 211(1):180-193, Epub Feb. 13, 2008.
Wang et al., "Evaluation of biocompatibility of polypyrrole in vitro and in vivo," *J Biomed Mater Res A.*, 68(3):411-422, Mar. 1, 2004.
Wang et al., "In vivo evaluation of a novel electrically conductive polypyrrole/poly(D,L-lactide) composite and polypyrrole-coated poly(D,L-lactide-co-glycolide) membranes," *J Biomed Mater Res A.*, 70(1):28-38, Jul. 1, 2004.
Wang et al., "Photo-crosslinked poly(epsilon-caprolactone fumarate) networks for guided peripheral nerve regeneration: material properties and preliminary biological evaluations," *Acta Biomater.*, 5(5):1531-1542, Epub Jan. 7, 2009.
Wang, "Synthesis and characterizations of biodegradable and crosslinkable poly(e-caprolactone fumarate), poly(ethylene glycol fumarate), and their amphiphilic copolymer," *Biomaterials*, 27(6):832-841, Epub Aug. 15, 2005.
Wiggins "Design of bioabsorbable, amorphous polymer networks and composites," PhD Thesis Abstract, University of Southern Mississippi, Hattiesburg, MS, 1992 [retrieved on Mar. 12, 2014]. Retrieved from the Internet <URL: http://www.osti.gov/scitech/biblio/7153129>, 2 pages.
Xie et al., "Experimental investigation on the reliability of routine SEC-MALLS for the determination of absolute molecular weights in the oligomeric range," *Polymer*, 43(14):3973-3977, Jun. 2002.
Xie, De-Liang, et al., "The synthesis and characterization of novel carboxyl telechelic microspheres, the synthesis and characterization of novel carboxyl telechelic microspheres" *J. Applied Polymer Science*,68(2): 205-216, Apr. 11, 1998.
Yang et al. "The design of scaffolds for use in tissue engineering. Part I. Traditional factors," *Tissue Eng.*, 7(6):679-689, Dec. 2001.
Yao et al., "Small applied electric fields guide migration of hippocampal neurons," *J Cell Physiol.*, 216(2):527-535, Aug. 2008.
Yaszemski et al., "Clinical needs for bone tissue engineering technology," Ed. Davis, *Bone Engineering*, 541-547, 2000.

(56) References Cited

OTHER PUBLICATIONS

Zhang et al., "Electrically conductive biodegradable polymer composite for nerve regeneration: electricity-stimulated neurite outgrowth and axon regeneration," *Artif Organs.*, 31(1):13-22, Jan. 2007.
International Search Report and Written Opinion for PCT/US2005/040571, dated Jul. 13, 2006, 7 pages.
European Search Report and Written Opinion for EP App. No. 05851461.3, completed Oct. 5, 2010, 5 pages.
International Preliminary Report on Patentability for PCT/US2005/040571, dated May 15, 2007, 5 pages.
European Search Report and Written Opinion for EP App. No. 05851973, completed Jun. 9, 2010, 4 pages.
European Search Report and Written Opinion for EP App. No. 06748605, completed Jun. 8, 2010, 5 pages.
European Search Report and Written Opinion for EP App. No. 06751721, completed Apr. 14, 2009, 3 pages.
European Search Report for EP 1 664 168, Application No. EP 04 78 2412, dated Aug. 9, 2006, 2 pages.
European Search Report for EP App. No. 04777316, completed Mar. 3, 2008, 3 pages.
European Search Report for EP App. No. 04782412, completed Aug. 9, 2006, 2 pages.
International Preliminary Report on Patentability for PCT/US2004/021040, dated Jan. 3, 2006, 5 pages.
International Preliminary Report on Patentability for PCT/US2004/027926, dated Feb. 28, 2006, 4 pages.
International Preliminary Report on Patentability for PCT/US2005/042240, dated May 22, 2007, 5 pages.
International Preliminary Report on Patentability for PCT/US2006/010629, dated Sep. 25, 2007, 4 pages.
International Preliminary Report on Patentability for PCT/US2006/016156, dated Oct. 30, 2007, 8 pages.
International Search Report and Written Opinion for PCT/US2004/020842, dated Dec. 16, 2004, 5 pages.
International Search Report and Written Opinion for PCT/US2004/021040, dated Dec. 15, 2005, 5 pages.
International Search Report and Written Opinion for PCT/US2004/027926, dated May 10, 2005, 4 pages.
International Search Report and Written Opinion for PCT/US2005/042240, dated Jun. 21, 2006, 7 pages.
International Search Report and Written Opinion for PCT/US2006/010629, dated Aug. 24, 2006, 4 pages.
International Search Report and Written Opinion for PCT/US2006/016156 dated Sep. 18, 2006, 10 pages.
U.S. Appl. No. 10/562,777, filed Jul. 7, 2006, 2007/0043202, Feb. 22, 2007, Yaszemski, Abandoned.
U.S. Appl. No. 10/568,058, filed May 7, 2008, 2008/0206308, 39,688, Jabbari Abandoned.
U.S. Appl. No. 12/803,777, filed Jul. 6, 2010, Yaszemski, Abandoned.
U.S. Appl. No. 10/562,591, filed Jun. 13, 2006, U.S. Pat. No. 7,642,300, Jan. 5, 2010, Yaszemski, Issued.
U.S. Appl. No. 11/718,962, filed May 9, 2007, U.S. Pat. No. 7,816,461, Oct. 19, 2010, Wang, Issued.
U.S. Appl. No. 11/909,241, filed Sep. 11, 2009, U.S. Pat. No. 8,343,527, Jan. 1, 2013, Dadsetan, Issued.
U.S. Appl. No. 11/912,188, filed Jun. 20, 2008, U.S. Pat. No. 8,912,247, Dec. 16, 2014, Wang, Issued.
U.S. Appl. No. 11/718,906, filed Feb. 12, 2008, 2008/0194792, 39,674, Wang, Pending.
U.S. Appl. No. 12/925,182, filed Oct. 15, 2010, 2013/0331869, Dec. 12, 2013, Runge, Pending.

\* cited by examiner

Scheme 1.

Self-crosslinking process of PCLF.

PHOTOCROSSLINKABLE POLY(CAPROLACTONE FUMARATE)

CROSS-REFERENCES TO RELATED APPLICATIONS

This application is a divisional application of U.S. application Ser. No. 11/718,906 (now U.S. Pat. No. 9,255,178), filed Feb. 12, 2008, which is a National Stage application under 35 U.S.C. § 371 of International Application No. PCT/US2005/040571, filed Nov. 10, 2005, which claims priority from U.S. Provisional Patent application No. 60/627,079 filed Nov. 12, 2004.

STATEMENT REGARDING FEDERALLY SPONSORED RESEARCH

This invention was made with government support under AR045871 and EB003060 awarded by the National Institutes of Health. The government has certain rights in the invention.

BACKGROUND OF THE INVENTION

1. Field of the Invention

The present invention relates to photocrosslinkable, biodegradable polymeric materials that in one application can be injected and then hardened in situ to form scaffolds for tissue and/or skeletal reconstruction.

2. Description of the Related Art

The clinical needs for bone regeneration are diverse, and there are roughly 1,000,000 patients who have skeletal defects each year in the United States that require bone graft procedures to achieve union. These include applications arising from resection of primary and metastatic tumors, bone loss after skeletal trauma, primary and revision total joint arthroplasty with bone deficiency, spinal arthrodesis, and trabecular voids following osteoporotic insufficiency fractures. Current clinical decision making in the selection, preparation and application of bone graft materials often involves many factors. From a structural perspective, several decisions need to be addressed prior to deciding on a surgical management plan.

First, the type of bone lost must be determined. The defect may be trabecular bone, cortical bone, or a combination of both structural bone types. Second, the nature of the defect must be defined, whether it is contained and has a bony or soft tissue shell, or is non-contained and represents a segmental loss of bone continuity. Third, the size of the defect (size of trabecular voids or length of segmental defects) must be determined. Mechanical issues that enter into the graft selection decision include the skeletal location of the defect to be reconstructed and the anticipated loads in that location. In addition, biologic issues such as host co-morbidities (for example, diabetes) may all have an effect on the bone graft incorporation process. Finally, surgical issues that play a role in the selection of graft material include consideration regarding the size of the surgical access portal relative to the size of the defect.

Current clinical methods of treating skeletal defects involve bone transplantation or the use of other materials to restore continuity. Autologous bone graft has been the gold standard of bone replacement because it provides such essential elements as osteogenic cells, osteoinductive factors, and an osteoconductive matrix for healing. However, the limited supply of autograft bone, and donor site morbidity both restrict the spectrum of cases in which it can be used alone. Allograft bone, although available in abundant supply, has drawbacks that include reduced rates of graft incorporation compared to autograft bone, and the possibility of pathogen transfer from donor to host.

Metals provide immediate mechanical support at the defect site but exhibit less than ideal overall integration with host tissue and can eventually fail due to fatigue loading if the bone does not heal prior to fatigue failure of the metal. Ceramics, such as β-tricalcium phosphate (β-TCP) and hydroxyapatite are both osteoconductive, and have found clinical use as surface coatings on metal prostheses to enhance bonding of those prostheses to bone. In particulate form, they offer increased mechanical strength to polymeric composite materials primarily in compression, but are less effective in enhancing resistance to torsional and bending forces. Poly(methyl methacrylate) bone cement can be injected or molded and is sometimes used to fill both cavitary and segmental defects, such as those that result from the curettage of a giant cell tumor or from the resection of a vertebral body in metastatic disease to the spine, respectively. However, the temperature can rise up to 100° C. during the exothermic polymerization reaction, and the heat released risks local tissue injury. Additionally, poly (methyl methacrylate) is non-biodegradable and can thus accumulate fatigue damage with time and eventually undergo mechanical failure.

Synthetic biodegradable polymers may provide treatment options not currently available. These materials can be manufactured in virtually unlimited supply and the flexibility in their design allows the synthesis of a wide range of polymers with varying mechanical, biologic, degradation, and rheologic properties. For instance, their mechanical and degradation properties can be manipulated by changing the polymer molecular weight during synthesis, and can thus be tailored to fit a particular application. The injectable nature of the skeletal regeneration biomaterial would be ideal to fill defects with limited accessibility or irregular shape. For example, minimally invasive endoscopic techniques now in clinical use would allow the injectable form of the biomaterial to be inserted for posterolateral intertransverse process spinal fusion. This would decrease the surgical trauma from the extensive exposure and muscle stripping that must now be done to put the graft material into position. The injectable material could be placed into cancellous voids from periarticular fractures, osteoporotic spinal fractures, or bone cysts without creating a large access hole in the surrounding cortical bone. These clinical situations represent the motivation for the development of injectable biodegradable polymeric composite materials for bone tissue engineering.

Thus, biodegradable scaffolds that can be injected and crosslinked in situ to fill defects offer attractive additions to existing methods (see, Yaszemski et al., "Clinical needs for bone tissue engineering technology", in Bone Engineering, J. E. Davis, Ed. Toronto, Em Squared, 2000, pp. 541-547). Recently developed injectable materials have fulfilled many design criteria for diverse orthopedic applications. A candidate material of this type is poly(propylene fumarate) (PPF), an unsaturated linear polyester that can be modified or crosslinked through its fumarate double bonds. PPF degrades by simple hydrolysis of the ester bonds and the degradation time depends on polymer characteristics such as molecular weight, type of crosslinker, and crosslinking density. Although many efforts have been made to explore the applications of PPF-based materials, there are still many important limitations of this material. The propylene glycol in each repeating unit provides only one free rotating carbon-carbon bond that contributes to the rigidity of the PPF polymer chain. In addition, a crosslinker is needed to form crosslinked PPF networks via redox initiation, which may lead to cytotoxicity associated with unreacted crosslinking monomers.

Poly (ε-caprolactone) (PCL) is a well-known biodegradable polymer and FDA-approved for use as resorbable sutures. It has excellent biocompatibility and flexibility. PCL was recently studied as a potential material for a temporary joint spacer (Elfick, *Biomaterials*, 23, p. 4463-4467, 2002) and tissue-engineered skin (Ng, *Tissue Engineering*, 7, p. 441-455, 2001).

An injectable copolymer based on PCL and fumarate segments, poly(caprolactone fumarate) (PCLF) is described in PCT International Patent Application No. WO 2005/004811. Due to the presence of PCL unit, the PCLF chain is much more flexible than the PPF chain. This renders PCLF self-crosslinkable by redox initiation without the use of any crosslinker.

The previously developed PCLF, however, has a dark brown color due to the proton scavenger triethylamine used in the condensation reaction. Because of the dark color, UV light cannot go through the PCLF material to allow it to crosslink efficiently by photoinitiation. Photocrosslinking is the formation of a covalent linkage between two macromolecules or between two different parts of one macromolecule. Photocrosslinking allows in vivo curing, which provides great flexibility for the placement and handling of implantable polymers for surgeons. The main advantages of photocrosslinking over other crosslinking techniques are spatial and temporal control of the polymerization, fast curing rates at room temperature, and ease of fashioning and flexibility during implantation (see Anseth, *Nature Biotechnology*, 17, p. 156-159, 1999).

Therefore, there is a need for photocrosslinkable poly (caprolactone fumarate), and in particular there is a need for photocrosslinkable poly(caprolactone fumarate) that is useful as a biocompatible, bioresorbable, injectable, and in-situ hardening scaffold for tissue engineering applications.

SUMMARY OF THE INVENTION

The invention provides a colorless or light-colored poly (caprolactone fumarate) that it is self-crosslinkable by both redox initiation and photoinitiation. It is useful as an injectable material in various research and clinical applications. In addition, the colorless or light-colored poly(caprolactone fumarate) does not interfere with various cell and tissue staining techniques. Thus, the poly(caprolactone fumarate) according to the invention allows much greater visibility of cells and tissues for in vitro and in vivo assays.

These and other features, aspects, and advantages of the present invention will become better understood upon consideration of the following detailed description, drawings, and appended claims.

BRIEF DESCRIPTION OF THE DRAWINGS

FIG. 2 shows FTIR spectra of PCL530 and three PCLF macromers. FTIR means Fourier Transform Infrared Spectroscopy that is used to determine the chemical structure of the polymers. As marked in FIG. 2, the absorption peaks can be assigned to the chemical structure of the polymers herein.

FIG. 5 shows DSC curves of PCLF macromers and their PCL precursors. DSC means Differential Scanning Calorimetry which is used to determine melting temperature $T_m$, glass transition temperature $T_g$, and heat of fusion $\Delta H_m$ for polymers. The crystallinity $\chi_c$ of PCL in the copolymers can be calculated by the $\Delta H_m$ values of copolymers and completely crystalline PCL ($\Delta H_m^c$=135 J/g) and the composition φ of PCL using the equation of $\chi_c=[\Delta H_m/(\phi \Delta H_m^c)]\times 100\%$. See Brandrup, J.; Immergut, E. H. Eds. *Polymer Handbook*, 3rd ed.; Wiley: New York, 1989.

FIG. 7 shows TGA thermograms of PCLF macromers and their PCL precursors. TGA is thermogravimetric analysis which is used to determine the weight loss and the thermal degradation temperature $T_d$ when the temperature increases. It can be seen in FIG. 7 that the thermal stability of the PCLF530 is lower than those of the other two PCLF macromers; nevertheless, all the PCLF macromers show higher thermostability than their PCL precursors because of higher molecular weights.

DETAILED DESCRIPTION OF THE INVENTION

The invention provides a copolymer including caprolactone units and fumarate units wherein the copolymer is colorless or light-colored poly(caprolactone fumarate) so that the copolymer is self-crosslinkable by both redox initiation and photoinitiation. Preferably, the copolymer is clear when it is in solution or melt state. In one form, the copolymer has a number average molecular weight of 4000 daltons or greater.

A copolymer according to the invention can be prepared by reacting a poly(caprolactone) diol, and fumaric acid or a salt (preferably, fumaryl chloride) thereof in the presence of an alkali metal salt. Preferably, the alkali metal salt is an alkali metal carbonate, and most preferably, the alkali metal salt is potassium carbonate.

The invention also provides a photocrosslinkable, biodegradable material including a copolymer including caprolactone units and fumarate units according to the invention, and a photoinitiator. Example photoinitiators include benzoin and benzoin ether compounds, benzil ketal compounds, acetophenone compounds, aminoalkylphenone compounds, hydroxyalkylphenone compounds, acylphosphine oxides, acylphosphine sulfides, phenylglyoxylate compounds, benzophenone compounds, thioxanthone compounds, and mixtures thereof. In one example material, the photoinitiator is bisacylphosphinoxide.

The material may be an injectable bone substitute or an injectable bone cement. The injectable nature of the material allows for the filling of defects of limited accessibility or irregular shape. For example, minimally invasive endoscopic techniques now in clinical use may allow the injectable form of the material to be inserted for posterolateral intertransverse process spinal fusion. The injectable material could be placed into cancellous voids from periarticular fractures, osteoporotic spinal fractures, or bone cysts without creating a large access hole in the surrounding cortical bone.

With respect to the injectable nature of a copolymer according to the invention, the temperature range of injection can be broad, between the melting point of the mixture and the boiling point of the solvent used in the mixture. Normally the polymer mixture is injected at room temperature for convenience. For PPF, one component in the copolymer, the highest temperature during the crosslinking would be around 48° C., while polymethylmethacrylate, the currently used bone cement, may cause as high as 100° C. during crosslinking. Thus, PPF has advantages over polymethylmethacrylate. For the copolymers according to the invention, the temperature would be even lower than 48° C. because the content of fumarate group the only crosslinkable segment in copolymers, is lower than 10%.

Because the biodegradable material according to the invention is self-crosslinking, the material does not need to include a crosslinker. A crosslinker is typically used to help bridge the neighboring double bonds in crosslinking. Because the self-crosslinkable and/or photocrosslinkable, biodegradable material according to the invention does not need any crosslinkers, toxicity concerns in biomedical applications are minimized; however, a crosslinker can be used.

The material according to the invention is suitable for forming a scaffold for tissue regeneration. In one form, the material includes a porogen to allow for the formation of a porous scaffold. Suitable porogens include salt crystals (e.g., sodium chloride) that may be used in a salt leaching technique that forms a porous scaffold. Examples of this type of particle leaching technique can be found in U.S. Pat. Nos. 6,436,426, 6,379,962 and 5,514,378. The porogen may also be a hydrogel porogen as described in PCT International Publication No. WO 2005/020849. The choice of porogen may be dictated by the crosslinking process. Porogens can be used in making a photo-crosslinked film; however, it depends the physical properties and color of the porogen. Also, some porogens may block the UV light thereby make the photocrosslinking procedure inefficient. Thus, the photocrosslinkable, biodegradable material according to the invention may or may not include a porogen depending on the final product desired.

The material may further include particulate or fiber reinforcement materials. Hydroxyapatite is especially advantageous to serve as a reinforcement material because of its similarity in composition to bone mineral, bioactivity and promotion of cellular function, and osteoconductivity. The reinforcement materials may also include single-wall carbon nanotube.

The material may further include one or more bioactive agents. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics.

The self-crosslinkable and/or photocrosslinkable, biodegradable material may also include an accelerator. Non-limiting example accelerators include toluidines (such as N,N-diethyl-p-toluidine ("DET") and N,N-dimethyl-o-toluidine ("DMT")), acetyl phenylhydrazine, maleic acid, quinines (such as napthaquinone and anthraquinone), and alkyl mercaptans. Often, in a photocrosslinking process, an accelerator is not needed because the whole procedure is rather short (e.g., less than 30 minutes).

In another aspect, the invention provides a biocompatible scaffold for tissue regeneration. The scaffold includes a biodegradable matrix including a copolymer including caprolactone units and fumarate units wherein the copolymer is prepared by reacting a poly(caprolactone) diol and fumaric acid or a salt (preferably, fumaryl chloride) thereof in the presence of an alkali metal salt. The copolymer may have a number average molecular weight of 4000 daltons or greater. Preferably, the copolymer is clear in solution or melt state. The matrix may include particulate or fiber reinforcement materials such as hydroxyapatite. The matrix may include one or more bioactive agents. The scaffold may be porous.

In an example embodiment of this invention, we have made colorless or light-colored poly(caprolactone fumarate) using potassium carbonate as the proton scavenger. Furthermore, we have modified prior PCLF synthesis processes to make the time consumption much shorter and the molecular weights of the final products higher. The newly synthesized PCLF has been tested to show it is self-crosslinkable by both redox initiation and photoinitiation. It is potentially useful as an injectable material in various research and clinical applications. In addition, the dark color in the previously developed PCLF interferes with various cell and tissue staining techniques. We expect the new colorless PCLF will allow much greater visibility of cells and tissues for in vitro and in vivo assays.

The scaffold may be formed from a copolymer according to the invention using various techniques. For example, a block copolymer of poly(propylene fumarate) and poly(ε-caprolactone) according to the invention may be extruded, injection molded or compression molded into a scaffold. Alternatively, solid free-form fabrication methods may also be used to form the scaffold from a copolymer according to the invention. Non-limiting examples of solid free-form fabrication methods include stereo-lithography, selective laser sintering, ballistic particle manufacturing, fusion deposition modeling; and three dimensional printing. The macrostructure and porosity of the scaffold can be manipulated by controlling printing parameters, and these features can be designed and tailored using computer assisted design (CAD) for individual patients. U.S. Pat. Nos. 6,530,958, 5,869,170, 5,518,680 and 5,490,962 provide examples of solid free-form fabrication methods. See also, Hutmacher et al., "Scaffold-based tissue engineering: rationale for computer-aided design and solid free-form fabrication systems", *Trends in Biotech.* 2004, 22(7):354. These patents and publications and all other patents and publications cited herein are incorporated herein by reference.

The applications of the material extend beyond scaffolds and bone cement. The self-crosslinkable and/or photocrosslinkable, biodegradable material including a copolymer according to the invention is suitable as a crosslinkable polymer in many biomedical applications. Since it is crosslinkable, a micropatterned surface can be made using this material. The material can also form a polymer network with controlled swelling ratios in a variety of solvents which make the material a sorbent for organic solvents or a carrier for catalysts.

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a "bioresorbable" material is one that breaks down over a finite period of time due to the chemical/biological action of the body. By "injectable", we mean the copolymer may be delivered to a site by way of a medical syringe. By "self-crosslinkable", we mean the functional groups of a polymer according to the invention may crosslink with the functional groups of the same polymer or another polymer according to the invention without a crosslinker that forms crosslinks between the functional groups of a polymer according to the invention and the functional groups of the same or another polymer according to the invention. By "photocrosslinkable", we mean the functional groups of a copolymer according to the invention may crosslink with the functional groups of the same polymer or another copolymer according to the invention by application of photons (e.g., UV light) in the presence of a photoinitiator.

The term "molecular weight" in this specification refers to "weight average molecular weight" ($M_w = \Sigma_i N_i M_i^2 / \Sigma_i N_i M_i$). Although weight average molecular weight ($M_w$) can be determined in a variety of ways, with some differences in result depending upon the method employed, it is convenient to employ gel permeation chromatography. As used herein, the term "number average molecular weight" ($M_n$) refers to the total weight of all the molecules in a polymer sample divided by the total number of moles present ($M_n = \Sigma_i N_i M_i / \Sigma_i N_i$). Although number average molecular weight can be determined in a variety of ways, with some differences in result depending upon the method employed, it is convenient to employ gel permeation chromatography. As used herein, the term "polydispersity" (DPI in Table 1) refers to the ratio of a materials' "weight average molecular weight" divided by its "number average molecular weight" ($M_w/M_n$).

EXAMPLES

The following examples have been presented in order to further illustrate the invention and are not intended to limit the invention in any way.

Example 1

Synthesis of Poly(Caprolactone Fumarate) Macromer

Figure 1:
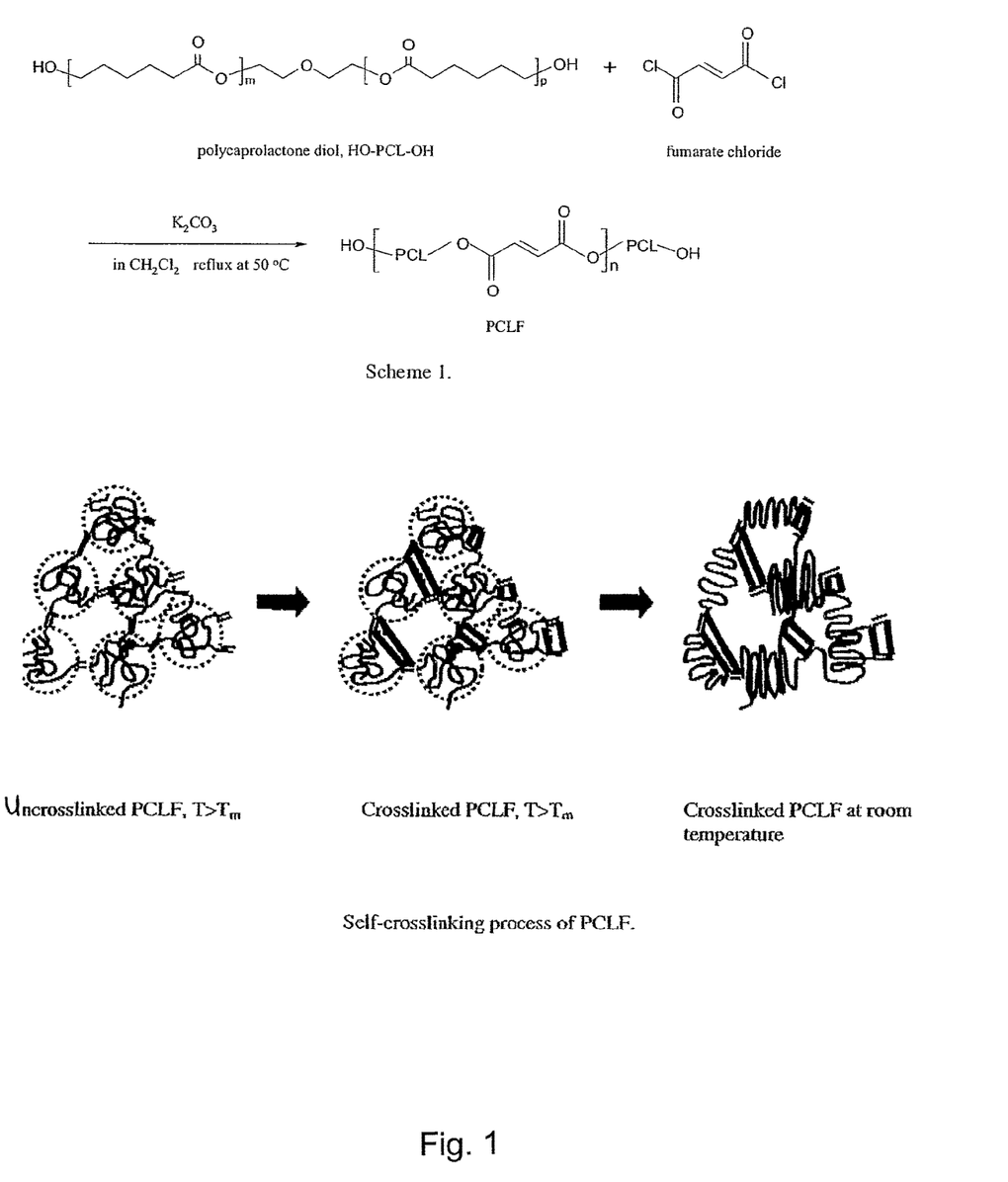
FIG. 1 shows a scheme for the synthesis of PCLF and a self-crosslinking process for PCLF.
Figure 2:
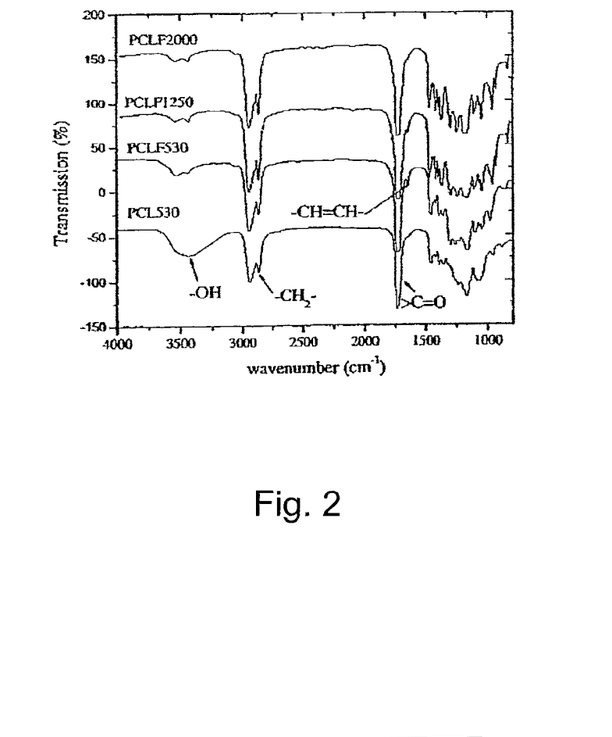
Figure 3:
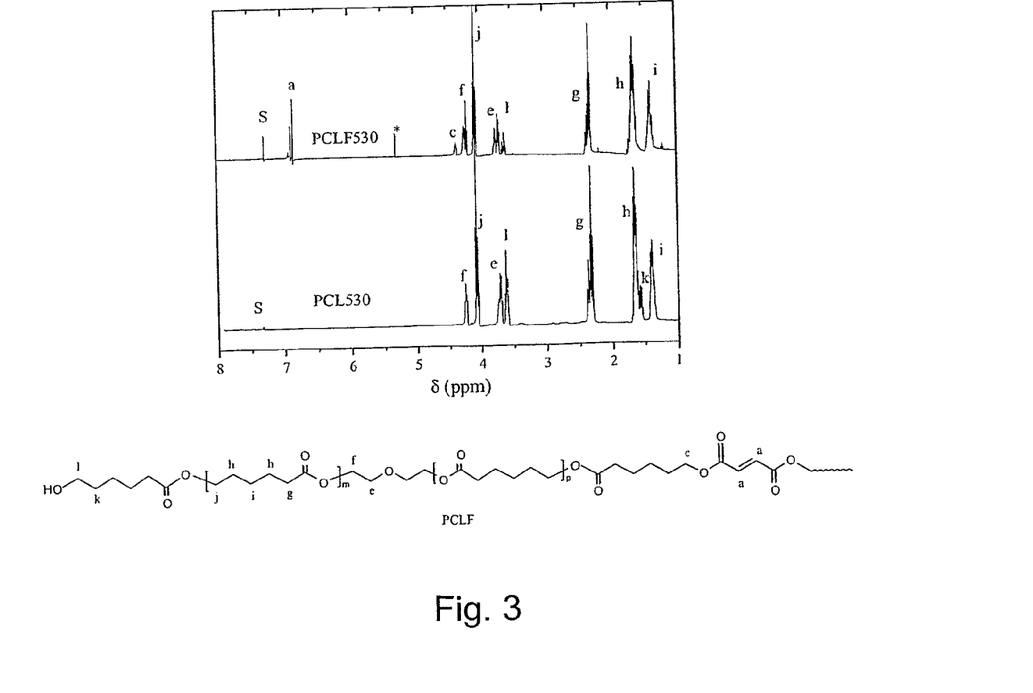
FIG. 3 shows $^1$H NMR (400.1 MHz, CDCl$_3$, reference TMS) spectra of PCL530 and PCLF530 where S=solvent and asterisks indicate signals due to methylene chloride. NMR means Nuclear Magnetic Resonance Spectroscopy which is used to determine the chemical structure of the polymers herein. All chemical shifts can be well assigned to different protons in the polymer backbone.
Figure 4:
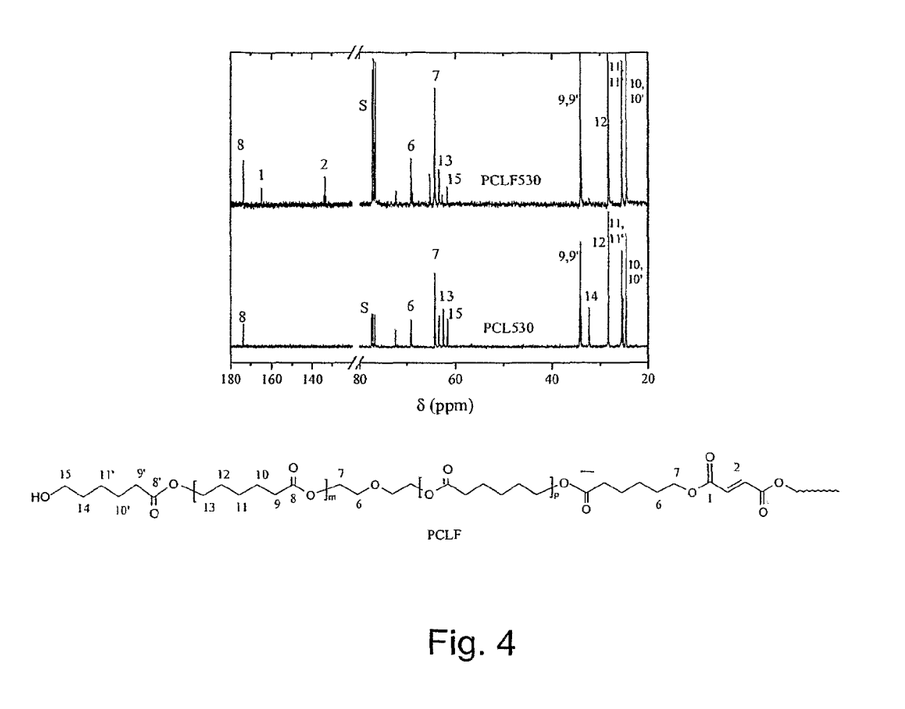
FIG. 4 shows $^{13}$C NMR (100.6 MHz, CDCl$_3$, reference TMS) spectra of PCL530 and PCLF530 where S=solvent.
Figure 5:
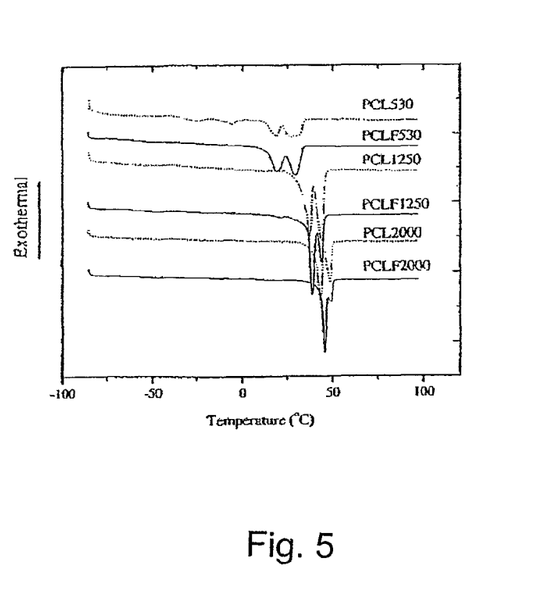
Figure 6:
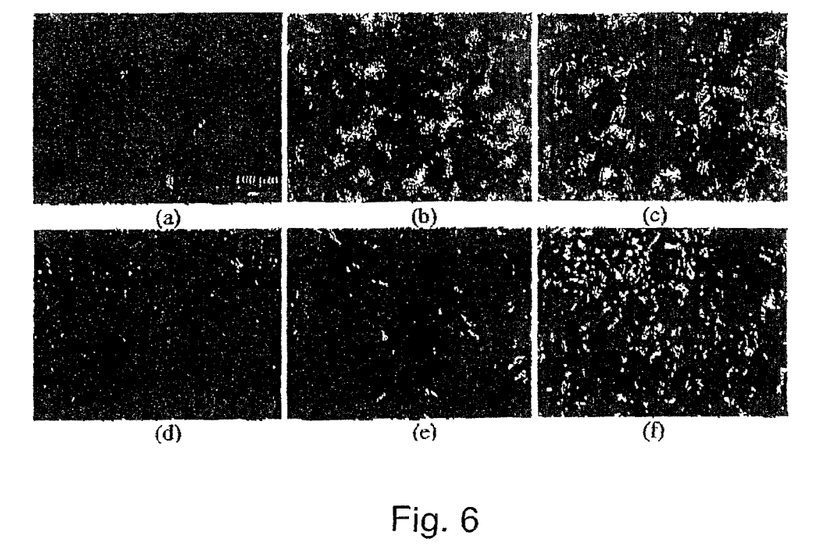
FIG. 6 shows polarized optical microscopic graphs of PCLF macromers (a, b, c: PCLF530, 1250, and 2000) and the corresponding PCL diols (d, e, f: PCL530, 1250, and 2000). (Magnification: 200×, scale bar in (a): 100 μm is applicable for all these six graphs).
Figure 7:
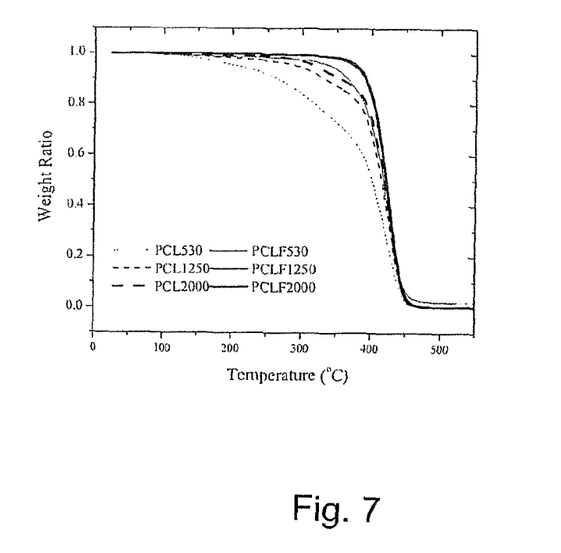
Figure 8:
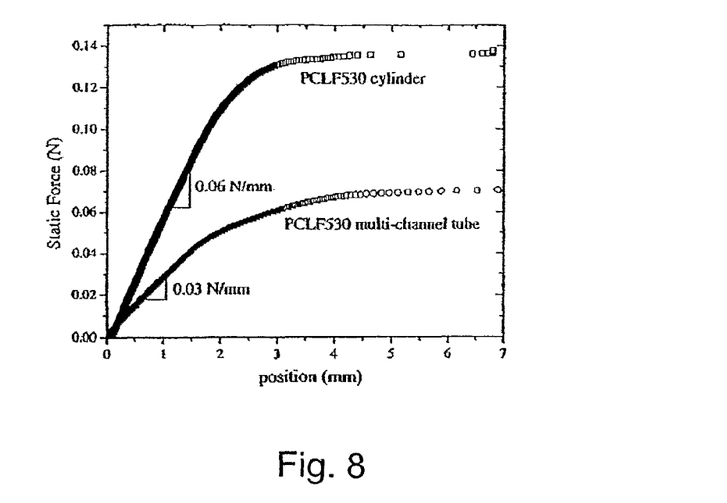
FIG. 8 shows typical force-deformation curves of a crosslinked PCLF530 multi-channel tube and a cylinder determined using DMA (Dynamic Mechanical Analyzer.
Figure 9:
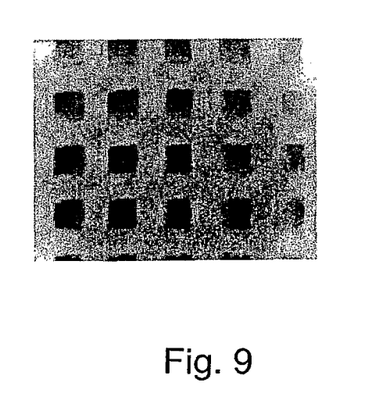
FIG. 9 shows a porous structure of one PCLF scaffold made using a 3D printing method.

A general synthesis scheme for poly(caprolactone fumarate) is shown in FIG. 1. PCL diols [α,ω-dihydroxy poly(ε-caprolactone)] with nominal molecular weights of 530, 1250, and 2000 g·mol$^{-1}$ were purchased from Aldrich Co. (Milwaukee, Wis.) and had the chemical structure as H—[O(CH$_2$)$_5$CO—]$_m$OCH$_2$CH$_2$—O—CH$_2$CH$_2$O[—OC(CH$_2$)$_5$O]$_n$—H. Prior to copolymerization, a certain amount of PCL diol was dried overnight in a vacuum oven at 50° C. All the other chemicals in the invention were also purchased from Aldrich Co. Methylene chloride was dried and distilled over calcium hydride before the reaction. Fumaryl chloride was purified by distillation at 161° C. Ground potassium carbonate was dried at 100° C. for 2 days and then cooled down at vacuum condition.

Fumaryl chloride, poly(ε-caprolactone) diol, and potassium carbonate were measured out in a 0.95:1:1.2 molar ratio. The PCL diol was dissolved in methylene chloride (1:2 by volume) and placed in a 1 L three-neck flask along with the powdered potassium carbonate. This mixture was stirred with an overhead mechanical stirrer to form a slurry. Fumaryl chloride dissolved methylene chloride (1:1 volume ratio) was added dropwise to the slurry. The reaction mixture was maintained at 50° C. under reflux using a condenser. After reacting for 12 hours, the mixture was cooled down and transferred to centrifuge tubes and spun down for 15 minutes at 4000 rpm until the potassium carbonate was completely removed. The supernatant was then added dropwise to petroleum ether to force the polymer out of solution, and the precipitate was rotary-evaporated to yield a wax-like product.

Characterizations

Gel Permeation Chromatography (GPC) was used to determine the molecular weight and polydispersity of the polymers herein. The GPC was carried out with a Waters 717 Plus autosampler GPC system (Waters, Milford, Mass., USA) connected to a model 515 HPLC pump and model 2410 refractive index detector. Fourier Transform Infrared Spectroscopy (FTIR) spectra were obtained on a Nicolet 550 spectrometer. All the polymers were analyzed using a zinc selenide ATR crystal. The resolution of the instrument was specified as 4 cm$^{-1}$ at a wavenumber of 1000 cm$^{-1}$. Proton and carbon Nuclear Magnetic Resonance (NMR) spectra were acquired on Varian Mercury Plus NMR spectrometer ($^1$H=400.1 MHz, $^{13}$C=100.6 MHz) using CDCl$_3$ solutions containing TMS. Differential Scanning Calorimetry (DSC) was measured on a TA Instruments DSC Q1000 differential scanning calorimeter at a heating rate of 10° C./min in a nitrogen atmosphere. To keep the same thermal history, each sample was preheated from room temperature to 100° C. and cooled to −90° C. at a cooling rate of 5° C./min. Then the DSC scan was recorded via heating from −90° C. to 100° C. In order to support the DSC results, the amorphous structure of the copolymers and the crystalline form of three PCL samples were observed using a Zeiss Axioskop Polarizing Optical Microscope (POM). Thermogravimetric Analysis (TGA) was done using a TA model Q500 thermal analyst. The TGA data were obtained in flowing nitrogen at a heating rate of 20° C./min. Intrinsic viscosities [η] of the polymers were measured in toluene at 30.0±0.05° C. with a calibrated Cannon Ubbehlobe capillary viscometer (Model OC, Cannon Instrument Co.) in water bath equipped with a Lauda ECO-Line Immersion Circulator (Brinkmann Co.). Toluene was distilled from CaH$_2$ before being used as the solvent.

Crosslinking Process and Scaffold Fabrication

A general crosslinking diagram is shown in FIG. 1.
Thermal-crosslinking process: Benzoyl peroxide (BPO) and N-dimethyl toluidine (DMT) were used as the free radical initiator and accelerator, respectively. A typical procedure for fabrication of scaffolds was as follows. One hundred microliters of initiator solution (50 mg of BPO in 250 microliters of 1-vinyl-2-pyrrolidinone (NVP)) and 40 microliters of accelerator solution (20 microliters of DMT in 980 microliters of methylene chloride) were added in 1.5 g PCLF solution in 500 microliters of methylene chloride and mixed thoroughly. The polymerizing scaffold was transferred into various Teflon molds, such as multi-channel tube mode. The mold was placed in a convection oven for overnight to facilitate crosslinking. After crosslinking, cylinders or tubes were removed from the mold before the mold was cooled to ambient temperature.

Photocrosslinking process: Photocrosslinking was initiated with ultraviolet (UV) (λ=380–315 nm) using a photoinitiator bisacylphosphinoxide (BAPO, Ciba Geigy). 75 μL of BAPO solution (30 mg BAPO in 150 μL methylene chloride) was added into 1.5 g PCLF solution in 500 microliters of methylene chloride and mixed thoroughly. The mixture was poured to a Petri dish and the Petri dish was placed directly under UV light for 30 minutes to facilitate crosslinking.

Scaffold fabrication: Similar crosslinking processes can be done to the mixture of PCLF and porogen (salt with various size distributions) to make scaffolds with different porosity, which can be controlled by the content of porogen. After crosslinking, salt was leached out by place the scaffolds in distilled water for 3 days, during which time water changes frequently. The scaffolds were dried in vacuum for at least 12 hours.

Characterizations of materials used and copolymers produced in the Examples are shown in FIGS. 2-9.

Table 1 below shows molecular characteristics and physical properties of PCL precursors, PCLF macromers, and their crosslinked products.

Thus, the invention provides photocrosslinkable, biodegradable poly(caprolactone fumarate) that in one application can be injected and then hardened in situ to form scaffolds for tissue and/or skeletal reconstruction.

INDUSTRIAL APPLICABILITY

The present invention relates to photocrosslinkable, biodegradable polymeric materials for forming scaffolds for tissue and/or skeletal reconstruction.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A photocrosslinkable, biodegradable composition comprising:
   poly(caprolactone fumarate);
   and a photoinitiator,
   wherein the poly(caprolactone fumarate) is colorless or light colored, and clear in the melt state.

2. The composition of claim 1, wherein the composition is injectable.

3. The composition of claim 1, wherein the composition is an injectable bone substitute.

4. The composition of claim 1, wherein, the composition is an injectable bone cement.

5. The composition of claim 1, further comprising a porogen.

6. The composition of claim 1, further comprising particulate or fiber reinforcement materials.

7. The composition of claim 1, wherein the composition does not include a crosslinker.

8. The composition of claim 1, wherein the photoinitiator is selected from the group consisting of benzoin and benzoin ether compounds, benzil ketal compounds, acetophenone compounds, aminoalkylphenone compounds, hydroxyalkylphenone compounds, acylphosphine oxides, acylphosphine sulfides, phenylglyoxylate compounds, benzophenone compounds, thioxanthone compounds, and mixtures thereof.

9. The composition of claim 1, wherein the poly(caprolactone fumarate) is prepared by reacting (i) a poly(ε-caprolactone) diol, and (ii) fumaric acid or a salt thereof.

10. The composition of claim 1, wherein the poly(caprolactone fumarate) is prepared by reacting (i) a poly(ε-caprolactone) diol, and (ii) fumaric acid or a salt thereof in the presence of an alkali metal salt.

11. The composition of claim 1, wherein the poly(caprolactone fumarate) is prepared by reacting (i) a poly(ε-caprolactone) diol, and (ii) fumaric acid or a salt thereof in the presence of an alkali metal carbonate.

12. The composition of claim 1, wherein the poly(caprolactone fumarate) is prepared by reacting (i) a poly(ε-caprolactone) diol, and (ii) fumaric acid or a salt thereof in the presence of potassium carbonate.

TABLE 1

| Polymer | $M_w$ (Dalton) | $M_n$ (Dalton) | DPI | % PCL (Wt. %) Feed Ratio | % PCL (Wt. %) NMR | $[\eta]$ (dL·g$^{-1}$) | $T_g$ (° C.) | $T_m$ (° C.) | $\Delta H_m$ (J/g) | $X_c$ (%) | $T_d$ (° C.) |
|---|---|---|---|---|---|---|---|---|---|---|---|
| PCL530 | 1270 | 770 | 1.65 | 100 | 100 | 0.04 | −80.6 | 26.2 | 52.2 | 38.6 | 354 |
| PCL1250 | 3030 | 1710 | 1.77 | 100 | 100 | 0.07 | −73.5 | 43.4 | 61.1 | 45.3 | 386 |
| PCL2000 | 5320 | 3970 | 1.34 | 100 | 100 | 0.11 | −68.5 | 48.7 | 76.7 | 56.8 | 392 |
| PCLF530a | 6050 | 3520 | 1.72 | 91.4 | 89.5 | — | −59.1 | 29.2 | 46.2 | 37.4 | 387 |
| PCLF530b | 6120 | 3450 | 1.77 | 91.0 | 89.3 | — | −61.0 | 29.2 | 46.7 | 38.0 | 392 |
| PCLF530c | 6100 | 3420 | 1.78 | 91.0 | 89.0 | 0.10 | −57.6 | 29.5 | 45.4 | 37.0 | 390 |
| PCLF1250 | 15800 | 9000 | 1.76 | 95.7 | 94.3 | 0.19 | −62.7 | 43.9 | 61.0 | 47.2 | 399 |
| PCLF2000 | 12900 | 7300 | 1.76 | 98.1 | 96.7 | 0.16 | −62.7 | 45.7 | 67.0 | 50.6 | 399 |
| Crosslinked PCLF530 | — | — | — | 91.0 | — | — | −54.5 | 27.5 | 1.27 | 0.01 | — |
| Crosslinked PCLF1250 | — | — | — | 95.7 | — | — | −58.5 | 35.7 | 26.8 | 20.7 | — |
| Crosslinked PCLF2000 | — | — | — | 98.1 | — | — | −58.7 | 43.1 | 47.1 | 35.6 | — |

13. The composition of claim 1, wherein the poly(caprolactone fumarate) is prepared by reacting (i) a poly(ε-caprolactone) diol, and (ii) a fumaryl halide.

14. The composition of claim 1, wherein the poly(caprolactone fumarate) is prepared by reacting (i) a poly(ε-caprolactone) diol, and (ii) fumaryl chloride.

15. The composition of claim 1, further comprising a bioactive agent selected from enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, therapeutics and mixtures thereof.

16. The composition of claim 1, wherein the copolymer was prepared by reacting (i) a poly(ε-caprolactone)diol and (ii) fumaric acid or a salt thereof in the presence of potassium carbonate to form a repeating polymer of polycaprolactone fumarate.

\* \* \* \* \*